United States Patent [19]
Kronner

[11] Patent Number: 5,549,563
[45] Date of Patent: Aug. 27, 1996

[54] REINFORCING INSERT FOR UTERINE MANIPULATOR

[76] Inventor: Richard F. Kronner, 1443 Upper Cleveland Rapids Rd., Roseburg, Oreg. 97470

[21] Appl. No.: 321,090

[22] Filed: Oct. 11, 1994

[51] Int. Cl.[6] ................................................. A61M 5/178
[52] U.S. Cl. ........................ 604/164; 604/264; 604/279; 604/280
[58] Field of Search .................................. 604/282, 1, 11, 604/286, 45, 49, 55, 96, 178, 164, 264, 271, 279; 128/898, 656; 606/193, 119

[56] References Cited

U.S. PATENT DOCUMENTS

| 3,860,006 | 1/1975 | Patel ........................................ 604/164 |
| 4,089,337 | 5/1978 | Kronner . |
| 4,430,076 | 2/1984 | Harris ........................................ 604/96 |
| 4,632,668 | 12/1986 | Wilson, Jr. et al. .................. 604/49 X |
| 4,775,362 | 10/1988 | Kronner . |
| 4,986,814 | 1/1991 | Burney et al. ...................... 604/264 X |

FOREIGN PATENT DOCUMENTS

2222951  3/1990  United Kingdom .................. 604/279

*Primary Examiner*—Corrine M. McDermott
*Assistant Examiner*—N. Kent Gring
*Attorney, Agent, or Firm*—Edward B. Anderson

[57] ABSTRACT

A stiffener device is usable with a uterine manipulator having a catheter tube and outer sheath. The catheter tube is formed in an arc and has an insertable end adapted to be inserted into the uterus. The sheath terminates in a flange that seats against the cervix. The catheter tube is stiffened by a stainless steel wire that is slightly less than the length of the tube, and terminates in a handle that provides for manual grasping to facilitate manipulation of the wire, and thereby the tube, while the insertable end of the tube is in the uterus. The handle may be a small loop formed as a continuation of the wire stiffener, or may be an elongate cylinder fixedly attached to the end of the wire stiffener. A latching assembly may be used to secure the handle adjacent to the outer tube opening.

1 Claim, 3 Drawing Sheets

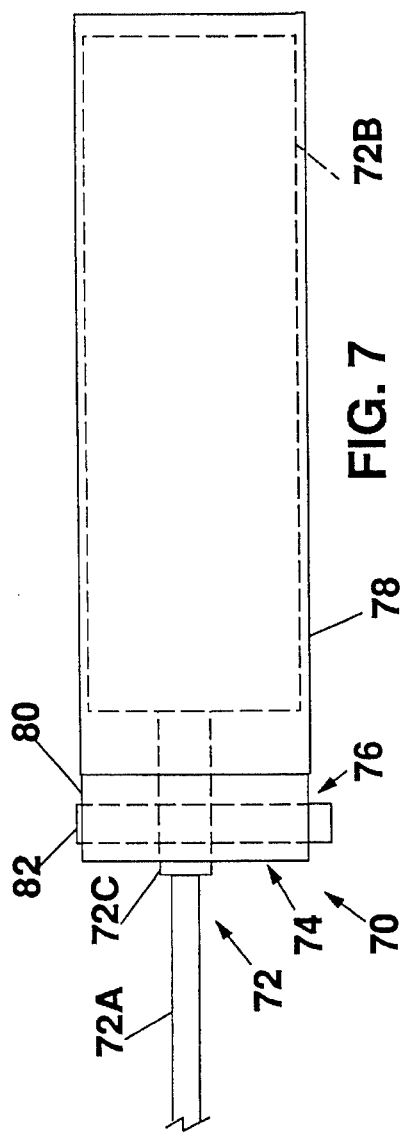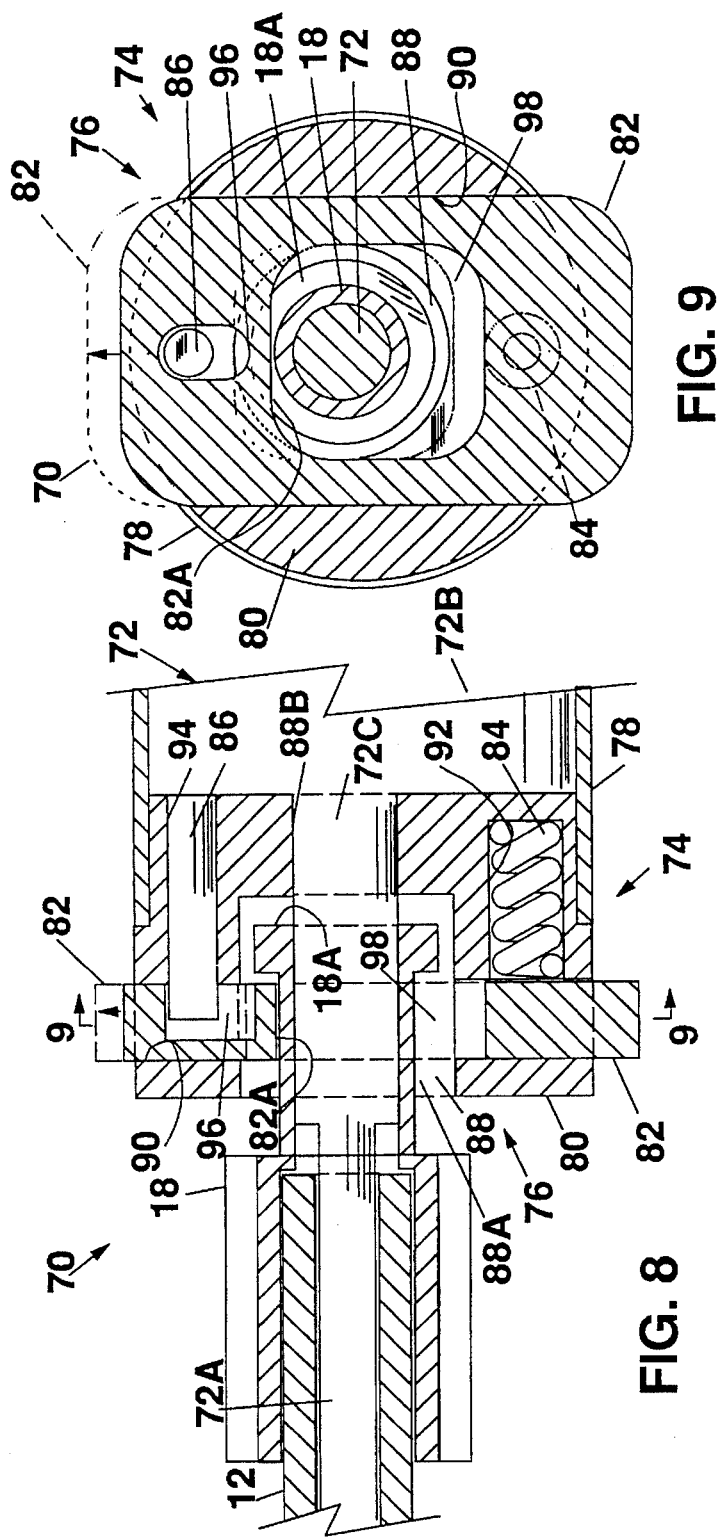

REINFORCING INSERT FOR UTERINE MANIPULATOR

BACKGROUND OF THE INVENTION

1. Field of the Invention

This invention relates to uterine manipulators, and more particularly to a reinforcing insert for a manipulator for providing increased stiffness to the manipulator during manual manipulation of the manipulator.

2. Related Art

A uterine manipulator is commonly used in properly positioning the uterus so that, for example, inaccessible areas may be viewed through a laparoscope extending through a small incision in the abdominal wall. A manipulator which includes an injector is usable for injecting fluids into the uterine cavity. This procedure is followed, for instance, in determining fallopian tube patency by noting the flow of an injected fluid from the uterus into the fallopian tubes.

One form of uterine manipulator is disclosed in U.S. Pat. No. 4,775,362. This manipulator is available commercially under the name Kronner Manipujector from UNIMAR, Inc. of Wilton, Conn.

This manipulator has a manually flexible elongate plastic tube formed in an arc with a radius of 5.5 inches. A wall encloses an elongate interior forming a primary passage, and has an insertable end, with an outlet port, adapted to be inserted through the cervical canal into the uterine cavity. An opposite end has an inlet port which locates outside the external opening of the vagina with the manipulator in place. A secondary passage extends therealong in the wall and has a charge port adjacent to its opposite end. The passage terminates in a discharge port adjacent to the insertable end, and serves to channel fluid introduced thereinto along the tube to the discharge port.

A balloon is mounted on the insertable end of the tube with the interior of the balloon communicating with the discharge port. The balloon is adapted to be inflated with fluid, typically a gas, channeled by the secondary passage.

An elongate plastic sheath has an internal passage that is open along one side for freely receiving the tube. The tube is thereby freely slidable relative to the sheath. Once inserted at a desirable position in the uterus, the tube may fixed in axial position relative to the sheath.

This manipulator is effective for injecting fluids into the uterus through the primary passage, typically when the cervix is sealed by an inflated balloon. It is also useful for positioning the uterus through manipulation of the tube. However, due to the flexibility of the tube, the tube often bends, making manipulation difficult. Procedures in which additional manipulative control is useful includes laparoscopic assisted hysterectomies, treatment of patients with severe adhesions, and other long-lasting laparoscopic procedures. In these procedures, the tube has enough flexibility to make manipulation difficult.

A uterine injector is a tube that is soft and flexible for patient comfort, and has a small hole in an insertable end that is used to inject fluids into a uterus after the entrance to the uterus is sealed by the inflation of a balloon attached near the insertable end. This device, also available from UNIMAR, Inc., is similar to the manipulator described in U.S. Pat. No. 4,089,337 except for the softness of the tube. Since the tube is so flexible it is difficult to properly insert into the cervical canal. A thin wire with a plastic coating and an S-shaped coil on one end for a handle has been used to provide sufficient stiffness to the tube to allow it to be inserted more easily into the uterus. Once the tube is inserted the wire is removed, since the only function of the tube is as an injector. Due to the softness and lack of shape of the tube, even with the wire inserted, the tube is not usable to manipulate the uterus.

SUMMARY OF THE INVENTION

The present invention overcomes the shortcomings of the existing manipulator-injector devices. The present invention generally provides for increasing the stiffness of the tube in the manipulator-injector for facilitating manipulation with the tube.

These features are provided in the present invention by a stiffener device comprising a rigid rod member and an attached handle. The rod member has an insertion end adapted to be freely inserted into and removed from the tube. The rod member also has a manipulation end opposite from the insertion end that extends externally from the tube inlet port when the insertion end is positioned in the tube. Since the rod member is stiffer than the tube, it effectively provides increased stiffness to the tube, permitting increased manipulation control.

A handle is attached fixedly to the insertion end of the rod member for facilitating manual manipulation of the rod member while the rod member is inserted in the tube. Forces applied to the rod member applies corresponding forces on the inserted end of the tube. Greater force can thereby be placed on the inserted end of the tube.

In one embodiment of the invention, the rod member is formed of stainless steel at spring temper. The handle, when made integrally with the rod member, is formed as a loop on the end of the rod member. When used with a manipulator that is formed in an arc, the rod member is preferably formed with the same arc shape. Compared to the basic plastic tube of the manipulator, the reinforcing insert of the invention substantially increases the effective stiffness of the tube. The insert may be removed after manipulation so that the tube can be used for introducing fluids into the uterus.

These and other features and advantages of the present invention will be apparent from the preferred embodiments described in the following detailed description and illustrated in the accompanying drawings.

BRIEF DESCRIPTION OF THE DRAWINGS

FIG. 7 is a partial side view of a second embodiment of a stiffener device made according to the invention.

FIG. 8 is an enlarged cross sectional view of a portion of the stiffener device of FIG. 7 in association with a tube and luhr lock coupling of the manipulator of FIG. 1.

FIG. 9 is a cross sectional view taken along line 9—9 in FIG. 8.

DETAILED DESCRIPTION OF THE PREFERRED EMBODIMENT

Figure 1:
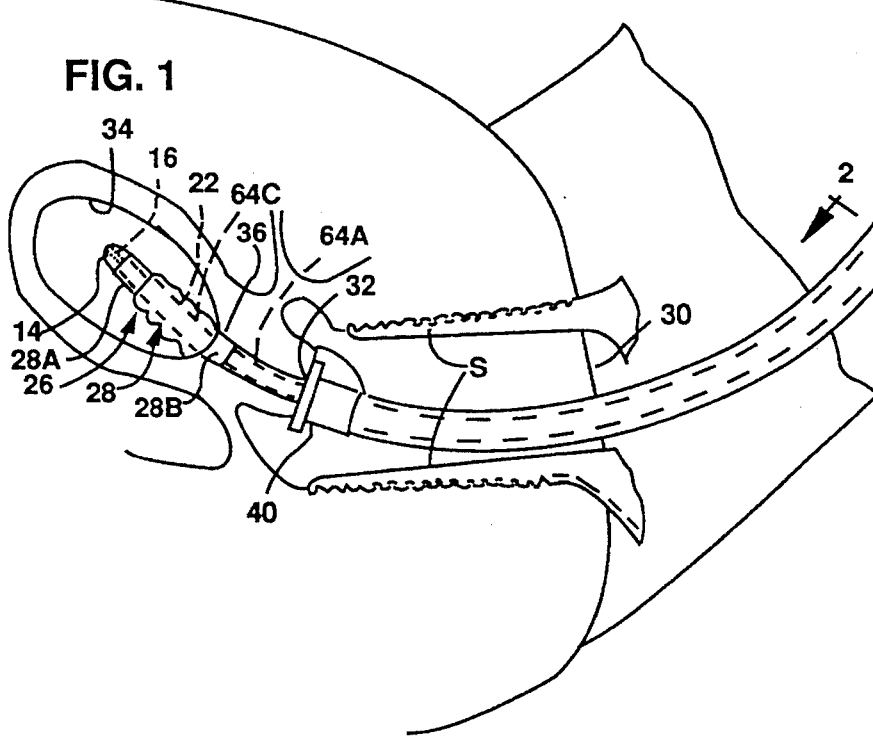
FIG. 1 is a view illustrating in a simplified manner the uterus of a patient, and a uterine manipulator as contemplated herein with a stiffener device made according to the invention.

Referring now to the drawings, a uterine manipulator constructed according to the invention is shown generally at 10. Manipulator 10 includes an elongate catheter tube portion 12 which extends the length of the manipulator. Such ordinarily may be made of a semi-rigid plastic material such as polyvinyl chloride. The insertable end of this tube, i.e. the end of the tube which is illustrated at the left in FIG. 1, is closed off with a rounded nose portion 14 provided with transversely extending ports 16 which connect with the interior of the tube. Joining with the opposite end (referred to herein as the exterior end) of the tube is a coupler 18 which enables the tube to be coupled with a syringe or other device actuatable to introduce fluid into the end of the tube. Coupler 18 is also commonly referred to as a luhr lock. The internal wall 13 of the tube defines a primary passage 19 extending the length of the tube for channeling fluid, introduced into the tube through coupler 18, along the length of the tube to be expelled through port 16.

Shown at 20 is an air line or tube which may be of a flexible plastic material and which enters catheter tube 12 adjacent to the latter's exterior end and connects with a secondary passage 21 extending along the length of the tube, passage 21 terminating at discharge port 22 formed in the side of tube 12 adjacent to the insertable end of tube 12. Fluid, i.e. air, is introduced into an air lo line 20 through a coupler 24 forming the inlet end or port of the air line. The coupler is provided to enable the easy attachment of a syringe or other air injector to the inlet end of the air line. Interposed the coupler and the air line is a pilot balloon 26, which on being expanded with air under pressure provides an indicator for indicating the degree of inflation that has occurred in an inflatable member, to be described.

Specifically, such inflatable member comprises a sleeve 28 of flexible resilient material mounted about the catheter tube 12 at the region of port 22 and with opposite end extremities 28A, 28B suitably secured to the catheter tube. The sleeve, in effect, forms a balloon which is extendable from the deflated state shown in FIG. 1 to an inflated state through the introduction of pressurized air to the interior of the sleeve.

In utilizing the manipulator of the invention, the insertable end of the manipulator is inserted through the external opening of the vagina indicated generally at 30 in FIG. 1 (with vaginal speculum S facilitating insertion), into the cervix or external opening of the cervical canal (shown at 32 in FIG. 1), through the cervical canal and into the uterine cavity of the uterus, shown at 34 in FIG. 1. The inflatable member or sleeve is inflated through the introduction of air and the manipulator retracted to bring the inflatable member into seated position against the region where the uterine cavity joins with the cervical canal, such being indicated at 36 in FIG. 1 and, for simplicity's sake, being referred to herein as the internal opening of the canal. To maintain such member in the seated position, a stop or abutment member movable along the catheter tube is brought up against the cervix, and the operator of the device does this through means accessible by the operator located outside the external opening of the vagina.

Further explaining, indicated at 40 is a stop or abutment member taking the form of a disc-shaped enlargement integrally joined to the end of an elongate sheath element 42. The sheath element is slotted along its length with slot 44, with this slot extending through stop 40. As can be seen with reference to FIG. 2, the passage 46 which extends along the interior of the sheath element and which receives the catheter tube 12 has a diameter which is significantly greater than the outer diameter of the catheter tube. As a consequence, there is essentially no frictional engagement between the sheath and the catheter tube, i.e., a non-clamping relationship exists, the passage 46 serving as a guide slot for tube 12 when such is axially shifted therealong. The passage also provides sufficient confinement for tube 12 whereby the sheath may function as a stiffening handle when used to manipulate tube 12.

Sheath element 42, adjacent to its end which is opposite the one having stop 40, referred to as the exterior end of the sheath element, is cut away as in region 48. The sheath element is made of a plastic, such as polyethylene, and the wall thickness of the sheath throughout most of the sheath is such as to impart a relatively stiff character through the sheath. In the cut away region, because of the reduced thickness that such results in, and because of the introduction of weakening slots such as the one shown at 50, a degree of flexible resilience is imparted to tab 52 relative to opposing side wall portion 54.

Integrally joined to side wall portion 54 and tab 52 are respective ones of a pair of opposed finger actuators 56 and 58. These extend outwardly to one side of the sheath and are laterally spaced apart from each other. Tab 52, where such is opposite side wall portion 54, has a screw 60 mounted thereon with its inner end protruding beyond the inner surface of tab 52 and forming a detent projecting toward the side of tube 12. The projection of the screw inwardly toward the tube is selected to be such that, without digital pressure applied to the actuators, the resilience inherent in the tab and side wall portion 54 will cause the screw end to bite into the side of the tube effectively clamping the sheath whereby such is held from axial displacement relative to tube 12. With finger pressure applied to actuators 56 and 58 outer extremities of the actuator move toward each other flexing the tab and side wall portion against the resilience of the sheath wall with the screw end moving clear of the side of tube 12. This releases the sheath for axial displacement relative to the tube. The tube and sheath both preferably have corresponding arc shapes, as shown. This arc has a nominal radius of about 5.5 inches to facilitate insertion in a uterus, with the exterior end extending upwardly for easier manipulation by an operator.

One of the primary functions of manipulator 10 is the use of tube 12 to manipulate the position of the uterus prior to or during a surgical procedure. Procedures in which additional manipulative control is useful includes laparoscopic assisted hysterectomies, treatment of patients with severe adhesions, and other long-lasting laparoscopic procedures. In these procedures, the desired manipulation is difficult to achieve because the tube flexes.

Figure 3:
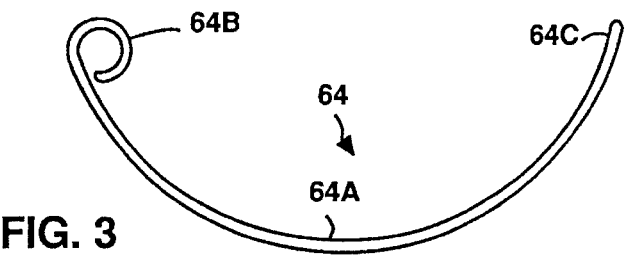
FIG. 3 is a side view of the stiffener device of FIG. 1.

In order to give tube 12 sufficient stiffness to allow manipulation of the uterus, a stiffener device 64 is used. FIG. 3 shows a side view of device 64. The stiffener device, in its preferred form, is made of type 302 stainless steel at spring temper. It is therefore essentially rigid compared to the stiffness of tube 12. The stainless steel is preferably passivated according to MIL Standard QQP 335C Type 6. Passivating removes oil and foreign matter from the device and provides a dull matte finish.

Stiffener device 64 includes a rod member 64A and an integral handle 64B. The end opposite from the handle is referred to as an insertion end 64C. These portions are formed of a single length of 0.085-inch outer diameter stock. Rod member 64A has a length slightly less than the length of tube 12, so that when handle 64B seats against coupler 18, insertion end 64C is just short of the insertable end of tube 12.

Coupler 18 is not a conventional luhr lock. A conventional luhr lock would be inserted into the exterior end of tube 12, and accordingly would have a very narrow passage that would not accommodate the insertion of rod member 64A. Coupler 18 therefore is a modified form of luhr lock that is inserted over the outside of the end of the tube, and has a passage sufficiently large to receive the rod member. This is shown more clearly in FIG. 8, which illustrates a second embodiment of a stiffening device described further below.

Figure 2:
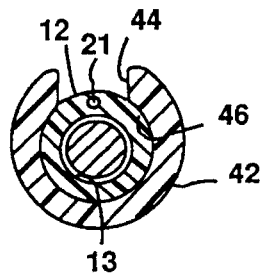
FIG. 2 is an enlarged cross-sectional view taken along line 2—2 in FIG. 1.
Figure 4:
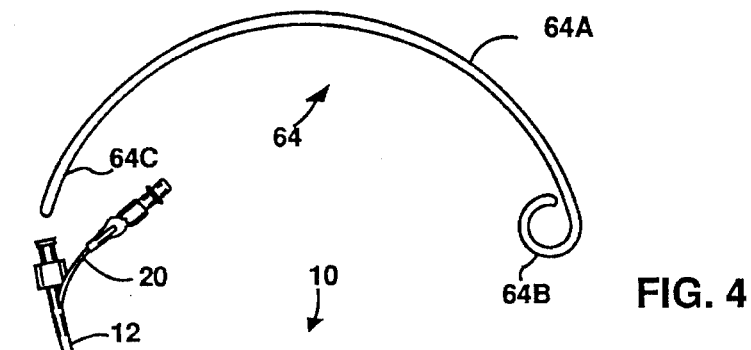
FIGS. 4–6 are further simplified illustrations showing the stiffener device of FIG. 3 being inserted in the uterine manipulator of FIG. 1.
Figure 5:
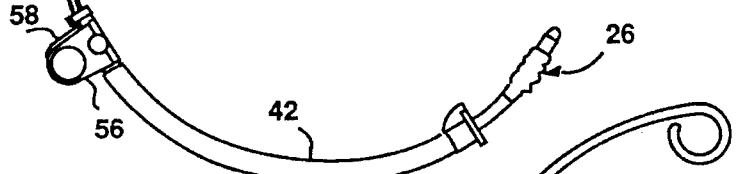
Figure 6:
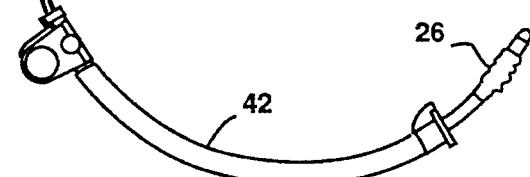
Figure 6:
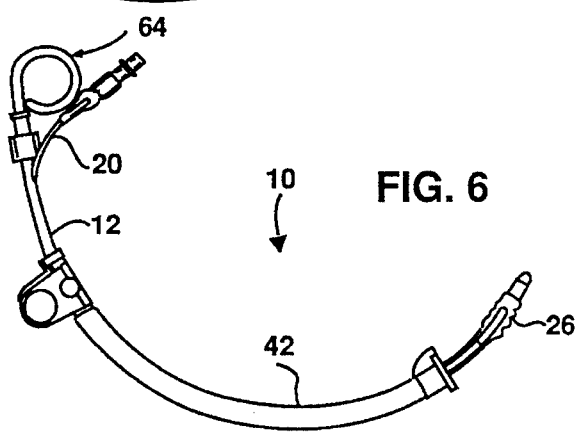

FIGS. 4–6 illustrate the steps of inserting rod member 64A in primary passage 19 of tube 12. As can be seen, the rod member has an arc shape that is of a curvature corresponding to that of tube 12. Also, the outer diameter of the rod member portion of the stiffener device is sized to be freely slidable in the tube, as is shown in FIG. 2.

Referring to FIG. 4, stiffener device 64 is oriented in alignment with the arc of the tube and with insertion end 64C adjacent to coupler 18. The insertion end is then inserted through coupler 18 and into passage 19. The rod member is shown partially inserted into the tube in FIG. 5. The rod member is preferably fully inserted into the tube so that the insertion end is inside the insertable end of the tube, as shown in FIG. 6, with the end of handle 64B positioned against coupler 18. The handle thus also acts as a stop to prevent inserting the rod member against the very end of the tube.

Stiffener element 64, as shown in FIG. 3, is an inexpensive embodiment of the invention. In this embodiment, handle 64B is formed simply as a loop in the plane of the arc of the rod member. The rod member is 12.75 inches long, and the loop forming the handle portion is about one inch in diameter. The handle portion is thus small enough to be readily grasped between the thumb and index finger during manipulation of the tube. By applying pressure on the handle sideways to the plane of the arc or in the line of the arc of the tube, the insertable end of the tube is readily manipulated inside the uterus.

It has been found that handle 64B of stiffening member 64 is somewhat difficult to manipulate due particularly to the small size of the wire and loop. A second embodiment of a stiffener apparatus 70 for use in catheter tube 12 is shown in FIGS. 7–9.

Apparatus 70 includes a stiffener device 72 and a latching device 74. Stiffener device 72 includes a rod member 72A constructed the same as rod member 64A. However, instead of handle 64B, device 72 has an elongate cylindrical handle 72B. This handle is preferably about 0.75 inches in diameter and 2.25 inches long, is hollow in order to reduce weight, and is made integrally with the rod member. An enlarged section of the rod member, formed as a luhr taper 72C, is located where the rod member attaches to the handle. As shown in FIG. 8 in particular, taper 72C seats in luhr lock 18.

Handle 72B is large enough, both in length and diameter, to be comfortably gripped in the palm of the hand for two to three hours at a time without tiring, as is often required during surgical procedures. Handle 64B of stiffening device 64 is small enough that it must be held between the thumb and fingers, which tire more easily than the hand grip used on handle 72B. Further, because the handle is cylindrical, it may be held in any orientation in the hand.

Stiffener device 72 may be used without latching device 74, described below. However, if the stiffener device is used without inserting the luhr taper into luhr lock 18, an increased bending moment is applied to the rod member at the point where it enters the luhr lock. Repeated use of the stiffener device in this way will result in failure of the rod member.

In order to facilitate the use of the handle with the luhr taper fully inserted into the luhr lock, latching device 74 is also preferably provided.

FIG. 7 thus shows a side view of the preferred embodiment of stiffener apparatus 70. FIG. 8 is a partial fragmentary longitudinal cross section showing apparatus 70 latched to luhr lock 18. FIG. 9 shows a lateral cross section taken along line 9—9 in FIG. 8.

Latching device 74 includes a latching assembly 76 attached to a cover 78 that completely encloses handle 72B and luhr taper 72C. Assembly 76 includes a body 80, a slide 82, a friction spring 84 and a limiter pin 86. The distal end of luhr lock 18 has a radially outwardly extending, circumferential lip 18A. Latching assembly 76 is manually operable for securing the luhr taper in the luhr lock by capturing the luhr lip relative to handle 72B.

Describing now latching assembly 76, body 80 has an inner passage 88 that includes an enlarged portion 88A, sized to receive the end of luhr lock 18, and a reduced portion 88B, sized to slidingly receive rod member 72A. Cover 78 is fixedly attached to the outer periphery of body 80, thereby securing latching assembly in position against handle 72B.

Body 80 also has a slot 90 extending laterally through it. Slot 90 is sized to slidingly receive slide 82. On opposite sides of and parallel with passage 88 are a spring bore 92 for receiving spring 84, and a pin bore 94 for receiving, in friction fit, pin 86. Pin bore 94 extends through the face of body 80 that is positioned adjacent to handle 72B. Spring bore 92 does not extend through this face, so that it instead has a bottom on which the spring is seated.

During assembly, the spring is positioned in bore 92 prior to positioning slide 82 in slot 90. After the slide is inserted in the slot, pin 86 is positioned in bore 94 with an end extending into slot 90. In order to accommodate the end of the pin, an oblong cavity 96 is formed in the associated portion of slide 82. Cavity 96 is sized to allow limited movement of the slide between a lock position, shown in solid lines in FIGS. 8 and 9, and a release position, shown in dashed lines. Spring 84 is in compression in bore 92, with the contact between the spring and the slide providing sufficient friction to hold the slide in either of the two slide positions, unless the slide is manually moved.

An opening 98 extends through the slide generally in line with enlarged inner passage 88, when the slide is in the release position. Slide 82 has an edge 82A that forms a boundary of opening 98 that is adjacent to pin cavity 96. When the slide is in the release position, opening 98 is positioned to allow the free insertion and removal of luhr lock 18 into enlarged inner passage 88. With the luhr lock in the inner passage, sliding slide 82 to the lock position causes slide edge 82A to be adjacent to the throat of the luhr lock and prevents the removal of lip 18A of the luhr lock.

With the slide in the lock position, luhr taper 72C cannot be removed from the throat of the luhr lock. This assures that when lateral force is applied to handle 72B during manipulation of tube 12, the lateral force is transferred from the handle, through the luhr taper to the luhr lock and tube. The rod member thereby has a much greater expected life before failure, since such forces are not applied directly to it.

Variations in form and detail may be made in the preferred embodiments described above without varying from the spirit and scope of the invention as defined in the claims when taken literally and as provided under the doctrine of equivalents. For instance, the rod member of the stiffener device may be made of any material that increases the effective stiffness of the manipulator tube. The handle can be any desired shape. The use of a handle latching device is optional and can also be designed in various ways to removably secure the handle to a manipulator tube. The preferred embodiments are thus provided for purposes of explanation and illustration, but not limitation.

I claim:

1. A uterine manipulator device comprising:

a manually flexible arc-shaped tube having a wall enclosing a tube passage, said tube having an insertable end, with an outlet port, adapted to be inserted through the cervical canal into the uterine cavity and an opposite end having an inlet port which locates outside the external opening of the vagina with said manipulator device in place, said tube passage serving to channel fluid introduced through said inlet port along the tube and out said outlet port;

a correspondingly arc-shaped plastic sheath having an internal sheath passage extending therealong, said tube being lodged within said sheath passage;

a rigid rod member having an arc shape the same as the arc-shape of the tube and an insertion end adapted to be freely inserted through said inlet port into said tube passage and a manipulation end opposite from said insertion end, said manipulation end extending externally from said tube inlet port when said insertion end is positioned in said insertable end of said tube; and handle means attached fixedly to said manipulation end for facilitating manual manipulation of said rod member.

* * * * *